US005661005A

United States Patent [19]
Shattil et al.

[11] Patent Number: 5,661,005
[45] Date of Patent: Aug. 26, 1997

[54] β3 INTEGRIN SUBUNIT SPECIFIC POLYPEPTIDES, CDNAS WHICH ENCODE THESE POLYPEPTIDES AND METHODS OF PRODUCING THESE POLYPEPTIDES

[75] Inventors: Sanford Shattil, Narberth, Pa.; Timothy O'Toole; Mark Ginsberg, both of San Diego, Calif.

[73] Assignees: Trustees of the University of Pennsylvania, Philadelphia, Pa.; Scripps Research Institute, La Jolla, Calif.

[21] Appl. No.: 597,583

[22] Filed: Feb. 2, 1996

Related U.S. Application Data

[62] Division of Ser. No. 338,009, Nov. 10, 1994, Pat. No. 5,585,463.

[51] Int. Cl.$^6$ .................................................... C12N 15/12
[52] U.S. Cl. .................. 435/69.1; 435/252.3; 435/320.1; 435/325; 536/23.5
[58] Field of Search .......................... 536/23.5; 435/320.1, 435/325, 69.1, 252.3

[56] References Cited

PUBLICATIONS

Alig et al., "Low Molecular Weight, Non–Peptide Fibrinogen Receptor Antagonists," *J. Med. Chem.* 1992, 35, 4393–4407.
Ausubel et al., *Current Protocols in Molecular Biology*, Wiley eds., New York 1990.
Bennett et al., "Exposure of Platelet Fibrinogen Receptors by ADP and Epinephrine," *J. Clin. Invest.* 1979, 64, 1393–4001.
Chen et al., "Ser–752–Pro Mutation in the Cytoplasmic Domain of Integrin β3 subunit and Defective Activation of Platelet Integrin $\alpha_{IIb}\beta_3$ (glycoprotein IIb–IIIa) in a Variant of Glanzmann Thrombasthenia," *Proc. Natl. Acad. Sci. USA* 1992, 89, 10169–10173.
Coller, "Antiplatelet Agents in the Prevention and Therapy of Thrombosis," *Annu. Rev. Med.* 1992, 43, 171–180.
Elledge et al., "λYES: a Multifunctional cDNA expression Vector for the Isolation of Genes by Complementation of Yeast and *Escherichia coli* Mutations," *Proc. Natl. Acad. Sci. USA* 1991, 88, 1731–1735.
Epic Investigators, "Use of a Monoclonal Antibody Directed Against the Platelet Glycoprotein IIb/IIIa Receptor in High–Risk Coronary Angioplasty," *New Engl. J. Med.*, 1994, 330, 956–961.
Fields et al., "A Novel Genetic System to Detect Protein–Protein Interactions," *Nature* 1989, 340, 245–246.
Frangione et al., "Solubilization and Purification of Enzymatically active Glutathione s–Transferase (pGEX) Fusion Proteins," *Anal. Biochem.* 1993, 210, 179–187.
Ginsberg et al., "Inside–Out Integrin Signalling," *Curr. Opin. Cell. Biol.* 1992, 4, 766–771.
Graber et al., "Evidence that Changes in Platelet Cyclic AMP Levels Regulate the Fibrinogen Receptor on Human Platelets," *J. Biol. Chem.* 1982, 257, 14606–14609.
Kohler et al., "Continuous Cultures of Fused Cells Secreting Antibody of Predefined Specificity," *Nature* 1975, 256, 495–497.
Kosbor et al., "The Production of Monoclonal Antibodies from Human Lymphocytes," *Immunology Today* 1983, 4, 72–79.
Otey et al., "An Interaction between α–Actinin and the $\beta_1$ Integrin Subunit In Vitro," *J. Cell Biol.* 1990, 111, 721–729.
Otey et al., "Mapping of the α–Actinin Binding Site within the $\beta_1$ Integrin Cytoplasmic Domain," *J. Biol. Chem.* 1993, 268, 21193–21197.
O'Toole et al., "Integrin Cytoplasmic Domains Mediate Inside–Out Signal Transduction," *J. Cell Biol.* 1994, 124, 1047–1059.
Plow et al., "The Effect of Arg–Gly–Asp–Containing Peptides on Fibrinogen and von Wellebrand Factor Binding to Platelets," *Proc. Natl. Acad. Sci. USA* 1985, 85, 8057–8061.
Plow et al., "Ligand Binding to GPIIb–IIIa: a Status Report," *Semin. Thromb. Hemost.* 1992, 18, 324–332.
Sastry et al., "Integrin Cytoplasmic Domains: Mediators of Cytoskeletal Linkages and Extra–and Intracellular Initiated Transmembrane Signaling," *Curr. Opin. Cell. Biol.* 1993, 5, 819–831.
Shattil et al., "Detection of Activated Platelets in Whole Blood Using Activation–Dependent Monoclonal Antibodies and Flow Cytometry," *Blood* 1987, 70, 307–315.
Sims et al., "Effect of Platelet Activation on the Conformation of the Plasma Membrane Glycoprotein IIb–IIIa Complex," *J. Biol. Chem.* 1991, 266, 7345–7352.
Smyth et al., "Regulation of Ligand Binding to Glycoprotein IIb–IIIa (integrin $\alpha_{IIb}\beta_3$) in Isolated Platelet Membranes," *Biochem. J.* 1993. 292, 749–758.

Primary Examiner—John Ulm
Assistant Examiner—Karen E. Brown
Attorney, Agent, or Firm—Law Offices of Jane Massey Licata

[57] ABSTRACT

$\beta_3$ integrin subunit specific polypeptides, cDNAs which encode these polypeptides and methods of producing these polypeptides are provided.

7 Claims, No Drawings

β3 INTEGRIN SUBUNIT SPECIFIC POLYPEPTIDES, CDNAS WHICH ENCODE THESE POLYPEPTIDES AND METHODS OF PRODUCING THESE POLYPEPTIDES

This is a division of application Ser. No. 08/338,009, filed Nov. 10, 1994, U.S. Pat. No. 5,585,463.

INTRODUCTION

This invention was made in the course of research sponsored by the National Institutes of Health. The U.S. Government may have certain rights in this invention.

BACKGROUND OF THE INVENTION

Intergrins are heterodimeric cell surface adhesion receptors which play an important role in normal and pathological processes including hemostasis and thrombosis. These receptors contain both an α and a β subunit. The integrin dimer has a cytoplasmic domain associated with the cytoskeleton. Thus, integrins form a critical connection between the extracellular matrix and the internal structural elements of a cell.

The most abundant integrin on platelets is $\alpha_{IIb}\beta_3$. $\alpha_{IIb}$ and $\beta_3$ are type I transmembrane glycoproteins that contain 1008 and 762 amino acids, respectively. These glycoproteins are complexed together in membranes as non-covalent heterodimers. More than 95% of each subunit is extracellular; each has a single transmembrane domain and a short cytoplasmic tail (20 amino acids in $\alpha_{IIb}$ and 47 amino acids in $\beta_3$).

$\alpha_{IIb}\beta_3$ mediates platelet aggregation as well as platelet adhesion and spreading on extracellular matrices. The affinity of this integrin for its extracellular ligands, arginine-glycine-aspartic acid (RDG)-containing ligands such as fibrinogen, yon Willebrand factor (vWf), fibronectin and vitronectin, is regulated by the cell by a process known as "inside-out" signaling. Binding of a ligand such as fibrinogen to $\alpha_{IIb}\beta_3$ initiates a cascade of signaling reactions necessary for full platelet adhesion. This process is referred to as "outside-in" signaling.

This regulation by the cell is an important feature of the ligand-receptor interaction. Platelets normally circulate in a resting state in which the apparent affinity of $\alpha_{IIb}\beta_3$ for ligands is low. When platelets enter a vascular wound or encounter a physiological agonist, such as thrombin or ADP, or an activator of protein kinase C, such as phorbol myristate acetate (PMA), affinity for the receptor is rapidly increased resulting in ligand binding and platelet aggregation. (Bennett, J. S. and Vilaire, G., J. Clin. Invest. 1979, 64, 1393). Platelet aggregation is initiated by the bridging of $\alpha_{IIb}\beta_3$ complexes on adjacent platelets by fibrinogen or vWf. This increase in affinity can be prevented or reversed by addition of compounds that result in increased amounts of intracellular cyclic AMP or cyclic GMP such as prostaglandin $I_2$ or nitric oxide, respectively. (Graber, S. E. and Hawiger, J., J. Biol. Chem. 1982, 257, 14606).

Platelet activation induces a conformational change in $\alpha_{IIb}\beta_3$, exposing a ligand-binding site that is likely to be composed of several discontinuous regions in the amino-terminal portions of both the $\alpha_{IIb}$ and the $\beta_3$ subunits. (Sims et al. J Biol Chem 1991, 266, 7345–7352; Plow et al. Semin Thromb Hemost 1992, 18, 324–332). Receptor affinity is believed to be regulated through cytoplasmic tails of the $\alpha_{IIb}\beta_3$. Substitution of the cytoplasmic domains of $\alpha_{IIb}\beta_3$ with those of $\alpha_5\beta_1$ in Chinese hamster ovary cells conferred an energy-dependent high affinity state on the extracellular portions of $\alpha_{IIb}\beta_3$. (O'Toole et al. J Cell Biol 1994, 124, 1047–1059). It is believed that intracellular signals generated by an agonist or antagonist result in modifications in the cytoplasmic domain of the $\alpha_{IIb}$ and $\beta_3$ subunits. These modifications lead to changes in the extracellular portion of the receptor that increase or decrease accessibility of the ligand binding site. (Ginsberg et al. Curt. Open. Cell. Biol. 1992, 4, 766). The study of recombinant forms of $\alpha_{IIb}\beta_3$ have shown that the affinity state of the fibrinogen receptor is influenced by sequences in the receptor's cytoplasmic tails in a cell type specific and energy-dependent manner. Thus, it has been suggested that specific cellular proteins interact with the tails and regulate receptor function. (O'Toole et al. J Cell Biol 1994, 124, 1047–1059).

Only a few intracellular proteins which interact with the cytoplasmic domains or tails of the $\alpha_{II}$ and $\beta_3$ subunits and regulate inside-out and outside-in signaling have been identified. Otey et al.(J Cell Biol 1990, 111, 721–729) demonstrated that α-actinin binds to the cytoplasmic domain of the β subunit of intact integrins from both the $\beta_1$ and $\beta_3$ subfamilies. They have also attempted to identify the binding site for α-actinin within the $\beta_1$ integrin cytoplasmic domain. (Otey et al. J. Biol. Chem. 1993, 268, 21193–21197).

Human cDNAs have now been identified which express $\beta_3$ integrin subunit specific polypeptides.

SUMMARY OF THE INVENTION

An object of the invention is to provide a $\beta_3$ integrin subunit specific polypeptide.

Another object of the invention is to provide a cDNA sequence which encodes a $\beta_3$ integrin subunit specific polypeptide.

Another object of the present invention is to provide an expression vector which comprises a DNA sequence which encodes a $\beta_3$ integrin subunit specific polypeptide. Cell lines transfected with this expression vector are also provided.

Another object of the present invention is to provide a method of making a $\beta_3$ integrin specific polypeptide by culturing a cell transfected with an expression vector containing a DNA which encodes a $\beta_3$ integrin specific polypeptide and recovering this polypeptide from the cell.

DETAILED DESCRIPTION OF THE INVENTION $\beta_3$ integrin subunit specific polypeptides, CDNAs which encode these polypeptides and methods of producing these polypeptides have now been found. These $\beta_3$ integrin subunit specific polypeptides of the present invention interact specifically with the $\beta_3$ subunit of integrin in vivo and are believed to regulate the adhesive and signaling functions of $\beta_3$ integrins. For the purpose of this invention a "$\beta_3$ integrin subunit specific polypeptide" is meant to include any polypeptide which interacts specifically with the $\beta_3$ integrin cytoplasmic tail encoded by a DNA sequence comprising a clone. By specifically it is meant that the polypeptides of the present invention interact preferentially with the $\beta_3$ integrin subunit as compared to the $\beta_2$ or $\alpha_{IIb}$ subunits. Specific interaction is demonstrated in vitro using, for example, a yeast system and a standard β-galactosidase assay suitable for analysis of yeast lysates.

A human cDNA clone (hereinafter referred to as "clone 28") has now been obtained through molecular cloning using a yeast two hybrid system. Clone 28, which was isolated from an Epstein Barr virus transformed human B-cell library, contains 723 base pairs (SEQ ID NO: 1) and encodes a $\beta_3$ integrin subunit specific polypeptide. cDNA similar to clone 28 have now been identified in a number of human tissues.

Clone 28 encodes a 95 amino acid $\beta_3$ integrin subunit specific polypeptide (SEQ ID NO: 2). In a preferred embodiment, the clone comprises clone 28 (SEQ ID NO: 1) which encodes a polypeptide, SEQ ID NO: 2. Specificity of the polypeptide for the $\beta_3$ integrin subunit can be demonstrated by several techniques. For example, specific interaction of SEQ ID NO:2 was demonstrated in the intracellular environment of a strain of yeast, Saccharomyces cervisiae. In the yeast system, clone 28 cDNA was fused to the 3' end of the activation domain of the GAL4 transcriptional activator. Interaction of the expressed fusion protein with a second fusion protein comprising the GAL4 binding domain and the $\beta_3$ cytoplasmic domain was then assessed by the transactivation of two reporter genes, HIS3 and lacZ, under the control of GAL 4. This protein-protein interaction was found to be a specific interaction meaning that there is no interaction of the polypeptide encoded by clone 28 with several unrelated control proteins also fused to the GAL4 DNA binding domain. Further, it was demonstrated that interaction of the clone 28-derived polypeptide with the $\beta_3$ cytoplasmic tail is decreased by mutating the $\beta_3$ tail. For example, mutation of a serine to a proline at amino acid residue 752 of the $\beta_3$ tail resulted in a 70% reduction in the interaction of the clone 28-derived polypeptide with the $\beta_3$ cytoplasmic tail. The strength of these binding interactions was measured using a quantitative $\beta$-galactosidase assay suitable for analysis of yeast lysates. (Ausubel et al., Current Protocols in Molecular Biology, Wiley, N.Y. 1990). This mutation of the $\beta_3$ cytoptasmic tail is known to be associated with defective adhesive and signaling functions of the integrin, both in a patient and in a heterologous system expressing recombinant integrin. (Chen et al. Proc Natl Acad Sci USA 1992, 89, 10169–10173; O'Toole et al. J. Cell Biol 1994, 124, 1047–1059).

Several forms of clone 28-related mRNA or cDNA have been found in human tissues. In Northern blot studies performed using standard Methods as described by Sambrook et al., (Molecular Cloning, Cold Spring Harbor Laboratory Press, 2nd edition, 1989), mRNA of approximately 1.1 to 1.2 kb was found in all human tissues examined including colon, blood leukocytes, prostate, testes, spleen, thymus and small intestine. In addition, using standard and 5'RACE PCR methods (Schuster et al. Focus 1992, 14, 46), larger clones encoding at least two different forms of cDNA have been identified in human cDNA libraries prepared from B lymphocyte, placenta and brain and by RT-PCR of an enriched preparation of platelets. One of these forms containing approximately 897 basepairs (SEQ ID NO: 3) encodes a $\beta_3$ integrin subunit specific polypeptide of the invention comprising about 111 amino acids (SEQ ID NO: 4).

The $\beta_3$ integrin subunit specific polypeptides of the present invention can be used in a variety of applications routine to one of skill in the art based upon this disclosure. Specifically, the $\beta_3$ integrin subunit specific polypeptides of the present invention can be used as immunogens to raise antibodies which are specific to the cloned peptides. Various procedures known in the art may be used for the production of antibodies to $\beta_3$ integrin subunit specific polypeptides. Such antibodies include, but are not limited to, polyclonal, monoclonal, chimeric, single chain, Fab fragments and an Fab expression library. For the production of antibodies, various host animals including, but not limited to rabbits, mice, and rats, are injected with a $\beta_3$ integrin subunit specific polypeptide. In one embodiment, the polypeptide or a fragment of the polypeptide capable of specific immunoactivity is conjugated to an immunogenic carrier. Adjuvants may also be administered in conjunction with the polypeptide to increase the immunologic response of the host animal. Examples of adjuvants which may be used include, but are not limited to, complete and incomplete Freund's, mineral gels such as aluminum hydroxide, surface active substances such as lysolecithin, pluronic polyols, polyanions, peptides, oil emulsions, keyhole limpet hemocyanin, and dinitrophenol.

Monoclonal antibodies to $\beta_3$ integrin subunit specific polypeptides of the present invention can be prepared using any technique which provides for the production of antibodies by continuous cell line in culture. Such techniques are well known to those of skill in the art and include, but are not limited to, the hybridoma technology originally described by Kohler and Milstein (Nature 1975, 256, 495–497), the human B-cell hybridoma technique described by Kosbor et al. (Immunology Today 1983, 4, 72) and the EBV-hybridoma technique described by Cole et al. (Monoclonal Antibodies and Cancer Therapy, Alan R. Liss, Inc., pp 77–96).

Antibodies immunoreactive to the polypeptides of the present invention can then be used to screen for the presence and subcellular distribution of similar polypeptides in biological samples. In addition, monoclonal antibodies specific to the $\beta_3$ integrin Subunit specific polypeptides of the present invention can be used as therapeutics. A monoclonal antibody directed against the platelet glycoprotein IIb/IIIa receptor is presently in clinical trials in high risk coronary angioplasty patients. (The Epic Investigator, New Engl J Med 1994, 330, 956–961).

The $\beta_3$ integrin subunit specific polypeptides can also serve as antigens useful in solid phase assays measuring the presence of antibodies which immunoreact with the claimed peptides. Solid phase competition assays can be used to measure immunological quantities of clone 28-related antigen in biological samples. This determination is not only useful in facilitating the complete characterization of the cellular function or functions of the $\beta_3$ integrin subunit specific polypeptides of the present inventions, but can also be used to identify patients with abnormal amounts of these proteins.

$\beta_3$ integrin subunit specific polypeptides of the present invention can also be used as capture reagents in affinity chromatography for the detection of proteins in addition to the $\beta_3$ integrin cytoplasmic domain that may become engaged in an intracellular macromolecular complex with integrins and to regulate adhesion receptor function. There is increasing evidence that such "signalling organelias" exist; however, there compositions are presently undetermined. (Sastry, S. K. and A. F. Horwitz, Curt Opin Cell Biol 1993, 5, 819–831). Affinity chromatography using $\beta_3$ integrin subunit specific polypeptides as the capture agent will facilitate characterization of these complexes.

In addition, these $\beta_3$ integrin subunit specific polypeptides are useful as reagents in an assay to identify candidate molecules which effect the interaction of the $\beta_3$ subunit and the cloned protein. Compounds that specifically block integrin activation without affecting other platelet responses have not yet been discovered. The screening process for such compounds is more complicated than that for inhibitors of ligand binding. For example, identification of inhibition of ligand binding has been facilitated by the finding that the RGD sequence is an integrin-recognition motif common to most $\alpha_{IIB}\beta_3$ ligands. (Plow, E. F. et al., Proc. Natl. Acad. Sci. USA 1985, 82, 8057) in contrast, the structural requirements for specific inhibition of activation of $\alpha_{IIB}\beta_3$ are unknown. Furthermore, studies of ligand binding to $\alpha_{IIB}\beta_3$ have been facilitated by the use of paraformaldehyde-fixed platelets and even activated forms of purified or recombinant $\alpha_{IIB}\beta_3$ (Shattil, J. S. et al., Blood 1987, 70, 307; Alig, L. et al., J. Med. Chem. 1992, 35, 4393; O'Toole, T. E. et al., J. Cell. Biol. 1994, 124, 1047). However, these forms of the receptor cannot be used to search for intracellular inhibitors of integrin activation because dynamic regulation of $\alpha_{IIB}\beta_3$ by agonists has been observed only in the intact, metabolically active platelet (Smyth, S. S. and Parise, L. V. Blochem. J. 1993, 292, 749). Use of the polypeptides of the present invention, however, can be used with permeabilized active platelets to screen potential integrin inhibitors and activators which compete with these $\beta_3$ integrin subunit specific polypeptides to interact specifically with $\alpha_{IIB}\beta_3$ integrin.

These $\beta_3$ integrin subunit specific polypeptides are also useful in acellular in vitro binding assays wherein alteration by a compound in the binding of these $\beta_3$ integrin subunit specific polypeptides to a $\beta_3$ integrin cytoplasmic tail is determined. Acellular assays are extremely useful in screening sizable numbers of compounds since these assays are cost effective and easier to perform than assays employing living cells. Upon disclosure of the polypeptides of the present invention, the development of these assays would be routine to the skilled artisan. In such assays, either the $\beta_3$ integrin subunit specific polypeptide or the $\beta_3$ integrin cytoplasmic tail is labeled. Such labels include, but are not limited to, radiolabels, antibodies, and fluorescent or ultraviolet tags. Binding of a $\beta_3$ integrin subunit specific polypeptide to the $\beta_3$ integrin cytoplasmic tail is first determined in the absence of any test compound. Compounds to be tested are then added to the assay to determine whether such compounds alter this interaction.

Compounds that inhibit activation of, or ligand binding to, $\alpha_{IIB}\beta_3$ are therapeutically useful in conditions associated with occlusive platelet thrombi, such as unstable angina, acute myocardial infarction, abrupt vascular occlusion after coronary angioplasty, or transient ischemic attacks. In fact, antibody, peptidic and non-peptidic inhibitors of fibrinogen binding to $\alpha_{IIB}\beta_3$ are currently undergoing clinical trials (The Epic Investigators, New Engl. J. Med. 1994, 330, 956). The effectiveness of these compounds as platelet aggregation inhibitors appears to be directly related to their ability to occupy $\alpha_{IIB}\beta_3$ and block ligand binding (Collet, B. S., Annu. Rev. Med. 1992, 43, 171).

Another advantage of the invention is its usefulness in screening for compounds that activate platelet integrin $\alpha_{IIB}\beta_3$ ligand binding. These compounds can be used in conditions associated with impaired blood coagulation such as in liver diseases which cause a reduction in clotting factors. The administration of a platelet integrin $\alpha_{IIB}\beta_3$ activator in such situations is useful to improve blood clotting under conditions of reduced availability of clotting factors.

In addition to providing a means for expressing $\beta_3$ integrin subunit specific polypeptides, the cDNAs of the present invention can also be used to clone the human chromosomal gene. Once a cDNA for a particular gene has been isolated it is within the routine skill of those in the art to clone the chromosomal gene. This is known as the genomic clone. Total chromosomal DNA is isolated and purified from any human tissue. The DNA is then cut into fairly large fragments by restriction enzymes, ligated into a suitable vector and then transformed into E. coli. Colonies are then allowed to form. A cDNA of the present invention is used as a probe for these colonies. The cDNA is first purified and then radiolabeled by nick translation. It is then contacted with the colonies. The cDNA only hybridizes with colonies containing the chromosoma gene of interest. The chromosomal gene is useful in a variety of assays including diagnosis of mutations in the gene. Integrins play an important role in normal and pathological processes including hemostasis and thrombosis. Such processes control normal cardiovascular function. Mutations in the gene which expresses integrins could result in abnormalities in these processes. Thus, genetic analysis may be used for the early diagnosis of patients at high risk for cardiovascular abnormalities. Early diagnosis and treatment of such abnormalities is useful in preventing myocardial infarction, strokes and other cardiovascular related maladies.

The following nonlimiting examples are provided to further illustrate the present invention.

EXAMPLES

Example 1: Identification and Isolation of Clone 28

Clone 28 was identified as a $\beta_3$ integrin subunit specific polypeptide using the yeast two-hybrid system as described by Fields et al. (Nature 1989, 340, 245). The GAL4 binding domain in the yeast vector, pGBT9 (Clontech, Palo Alto, Calif.), was fused at its 3' end to the $\beta_3$ cytoplasmic domain. An EBV-transformed B cell cDNA library was obtained and fused to the 3' end of the GAL4 activation domain in the yeast vector, pACT (Elledge et al. Proc Natl Acad Sci USA 1991, 88, 1731). The yeast strain Y-190 was sequentially transformed with these vectors and the yeast grown under conditions or Trp, Leu and His auxotrophy. Yeast colonies able to overcome this auxotrophy were the screened for expression of β-galactosidase activity on filter lifts and individual transformants were subsequently analyzed by quantitative β-galactosidase activity. Quantitative β-galactosidase activity correlates with the strength of the interaction in yeast between the $\beta_3$ cytoplasmic domain and an interacting polypeptide whose cDNA was originally present in the $\beta_3$ cell library. Of 1.5 million independent yeast transformants in the initial library screen, five were strikingly positive for β-galactosidase activity. All five were identical to clone 28 (SEQ ID NO:1).

Example 2: Expression of $\beta_3$ Integrin Subunit Specific Polypeptide

SEQ ID NO: 2, the polypeptide encoded by clone 28, was expressed as a GST fusion protein in E. coli and then cleaved from the GST. The polypeptide was then purified in accordance with procedures described by Frangione et al. Anal Biochem 1993, 210, 179. The purified polypeptide was used in the preparation of monoclonal and polyclonal antibodies.

Example 3: Determination of Specificity to the $\beta_3$ Subunit

The specificity of the polypeptides of the present invention for the $\beta_3$ cytoplasmic domain was determined in yeast using the quantitative β-galactosidase assay. Results from a series of these assays demonstrate that SEQ ID NO: 2 and SEQ ID NO: 4 bind avidly to the $\beta_3$ cytoplasmic domain. In sharp contrast, these polypeptides did not bind significantly to either the integrin $\beta_1$ or $\beta_2$ cytoplasmic domains, nor did they bind to irrelevant proteins fused to the GAL4 binding domain. In addition, the $\beta_3$ cytoplasmic domain does not bind to nonspecific fusion proteins such as SV40 large T antigen or the integrin $\alpha_{IIb}$ subunit. Accordingly, these experiments establish the consistency and specificity of the interaction of the polypeptides of the present invention and the $\beta_3$ cytoplasmic domain.

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
        ( A ) LENGTH: 723
        ( B ) TYPE: Nucleic Acid
        ( C ) STRANDEDNESS: Single
        ( D ) TOPOLOGY: Linear ( i v ) ANTI-SENSE: NO ( x i ) SEQUENCE DESCRIPTION: SEQ ID NO: 1:

```
GGCCACGAAG  GCCCAAAAAT  CACAAGGAAG  AAAAGTGTTA  TAACTTATTC   50
TCCAACAACT  GGAACTTGTC  AAATGAGTCT  ATTTGCTTCT  CCCACAAGTT  100
CTGAAGAGCA  AAAGCACAGA  AATGGACTAT  CAAATGAAAA  GAGAAAAAA   150
TTGAATCACC  CCAGTTTAAC  TGAAAGCAAA  GAATCTACAA  CAAAAGACAA  200
TGATGAATTC  ATGATGTTGC  TATCAAAAGT  TGAGAAATTG  TCAGAAGAA   250
TCATGGAGAT  AATGCAAAAT  TTAAGTAGTA  TACAGTGACA  AAAGTGAATA  300
AACAAAAACT  GTTTGAAAAG  AGTACAGGAC  TTCCTCACAA  AGCATCACGT  350
CATCTTGACA  GCTATGAATT  CCTTAAAGCC  ATTTTAAACT  GAGGCATTAA  400
GAAGAAATGC  ACTCACCATG  AGCACCAACT  TCTGCATCTG  CCTGATCATA  450
TTTAAAGGAA  CAGAGAAATA  TTTGTAATTA  ATCTGCCCAG  TAAATACCAG  500
CTCGTAGCAG  TTGGCAGGTG  CATGTCTAGA  TAAAATTTCT  TGCAGCTAAT  550
TTAAACTTTC  TAACCGCACC  AGTAGATAAT  CTCAATGTAA  ATAATACATT  600
TCTTCTTGGC  TCTTTAATGT  AAGCCAACAT  GGAGAGGAAG  ATCTTGACTT  650
ATATTCTGTA  CCACATACAC  TTCTGTGGAC  TTTTAGCATT  TGTGGGTAGA  700
CTTAATGGCC  TTCGTGGCCT  CGA                                723
```

( 2 ) INFORMATION FOR SEQ ID NO: 2:

( i ) SEQUENCE CHARACTERISTICS:
        ( A ) LENGTH: 95
        ( B ) TYPE: Amino Acid
        ( D ) TOPOLOGY: Linear ( x i ) SEQUENCE DESCRIPTION: SEQ ID NO: 2:

```
GLY  HIS  GLU  GLY  PRO  LYS  ILE  THR  ARG  LYS  LYS  SER  VAL  ILE  THR
                  5                   10                      15
TYR  SER  PRO  THR  THR  GLY  THR  CYS  GLN  MET  SER  LEU  PHE  ALA  SER
                 20                   25                      30
PRO  THR  SER  SER  GLU  GLU  GLN  LYS  HIS  ARG  ASN  GLY  LEU  SER  ASN
                 35                   40                      45
GLU  LYS  ARG  LYS  LYS  LEU  ASN  HIS  PRO  SER  LEU  THR  GLU  SER  LYS
                 50                   55                      60
GLU  SER  THR  THR  LYS  ASP  ASN  ASP  GLU  PHE  MET  MET  LEU  LEU  SER
                 65                   70                      75
```

LYS VAL GLU LYS LEU SER GLU GLU ILE MET GLU ILE MET GLN ASN
                80                      85                      90
LEU SER SER ILE GLN
                95

( 2 ) INFORMATION FOR SEQ ID NO: 3:

( i ) SEQUENCE CHARACTERISTICS:
        ( A ) LENGTH: 897
        ( B ) TYPE: Nucleic Acid
        ( C ) STRANDEDNESS: Single
        ( D ) TOPOLOGY: Linear ( i v ) ANTI-SENSE: NO ( x i ) SEQUENCE DESCRIPTION: SEQ ID NO: 3:

```
CTGGTTCGGC CCACCTCTGA AGGTTCCAGA ATCGATAGTG AATTCGTGGT 50
TTCCTTTGGC GGATTTTCTG TTTTCGGAAG TTGCTGGGTT CGTTTTATTC 100
AGCGGCAGTG GTGCTTTCCC GAATCTCAGA ATGCCTGTTA AAGATCACT  150
GAAGTTGGAT GGTCTGTTAG AAGAAAATTC ATTTGATCCT TCAAAAATCA 200
CAAGGAAGAA AAGTGTTATA ACTTATTCTC CAACAACTGG AACTTGTCAA 250
ATGAGTCTAT TTGCTTCTCC CACAAGTTCT GAAGAGCAAA AGCACAGAAA 300
TGGACTATCA AATGAAAAGA GAAAAAAATT GAATCACCCC AGTTTAACTG 350
AAAGCAAAGA ATCTACAACA AAAGACAATG ATGAATTCAT GATGTTGCTA 400
TCAAAAGTTG AGAAATTGTC AGAAGAAATC ATGGAGATAA TGCAAAATTT 450
AAGTAGTATA CAGTGACAAA AGTGAATAAA CAAAAACTGT TTGAAAAGAG 500
TACAGGACTT CCTCACAAAG CATCACGTCA TCTTGACAGC TATGAATTCC 550
TTAAAGCCAT TTTAAACTGA GGCATTAAGA AGAAATGCAC TCACCATGAG 600
CACCAACTTC TGCATCTGCC TGATCATATT TAAAGGAACA GAGAAATATT 650
TGTAATTAAT CTGCCCAGTA AATACCAGCT CGTAGCAGTT GGCAGGTGCA 700
TGTCTAGATA AAATTTCTTG CAGCTAATTT AAACTTTCTA CACGCACCAG 750
TAGATAATCT CAATGTAAAT AATACATTTC TTCTTGGCTC TTTAATGTAA 800
GCCAACATGG AGAGGAAGAT CTTGACTTAT ATTCTGTACC ACATACACTT 850
CTGTGGACTT TTAGCATTTG TGGGTAGACT TAATGGCCTT CGTGGCC     897
```

( 2 ) INFORMATION FOR SEQ ID NO: 4:

( i ) SEQUENCE CHARACTERISTICS:
        ( A ) LENGTH: 111
        ( B ) TYPE: Amino Acid
        ( D ) TOPOLOGY: Linear ( x i ) SEQUENCE DESCRIPTION: SEQ ID NO: 4:

Met Pro Val Lys Arg Ser Leu Lys Leu Asp Gly Leu Leu Glu Glu
                5                   10                  15

Asn Ser Phe Asp Pro Ser Lys Ile Thr Arg Lys Lys Ser Val Ile
                20                  25                  30

Thr Tyr Ser Pro Thr Thr Gly Thr Cys Gln Met Ser Leu Phe Ala
                35                  40                  45

Ser Pro Thr Ser Ser Glu Glu Gln Lys His Arg Asn Gly Leu Ser
                50                  55                  60

Asn Glu Lys Arg Lys Lys Leu Asn His Pro Ser Leu Thr Glu Ser
                65                  70                  75

Lys Glu Ser Thr Thr Lys Asp Asn Asp Glu Phe Met Met Leu Leu

|  | 80 | 85 | 90 |
|---|---|---|---|
| Ser Lys Val Glu | Lys Leu Ser Glu Glu<br>95 | Ile Met Glu Ile Met<br>100 | Gln<br>105 |
| Asn Leu Ser Ser | Ile Gln<br>110 | | |

What is claimed is:

1. A purified and isolated cDNA encoding a human $\beta_3$ integrin subunit specific polypeptide, which polypeptide comprises SEQ ID NO: 2 or 4.

2. The cDNA of claim 1 comprising SEQ ID NO: 1 or 3.

3. An expression vector comprising a DNA sequence encoding a $\beta_3$ integrin subunit specific polypeptide, which polypeptide comprises SEQ ID NO: 2 or 4.

4. The expression vector of claim 3 wherein the DNA sequence comprises SEQ ID NO: 1 or 3.

5. A cell line transfected with the expression vector of claim 3 or claim 4.

6. A method of making a $\beta_3$ integrin subunit specific polypeptide comprising:

culturing a cell transfected by an expression vector comprising DNA encoding a $\beta_3$ integrin subunit specific polypeptide, which polypeptide comprises SEQ ID NO: 2 or 4; and recovering the $\beta_3$ integrin subunit specific polypeptide from the cell.

7. The method of claim 6 where the DNA comprises SEQ ID NO: 1 or 3.

* * * * *

UNITED STATES PATENT AND TRADEMARK OFFICE
CERTIFICATE OF CORRECTION

PATENT NO. : 5,661,005

DATED : Aug. 26, 1997

INVENTOR(S) : Shattil et al.

It is certified that error appears in the above-indentified patent and that said Letters Patent is hereby corrected as shown below:

At col. 1, line 36, please delete "yon" and insert therefor --von--.

At col 4, line 55, please delete "Curt" and insert therefor --Curr--.

Signed and Sealed this

Thirtieth Day of December, 1997

Attest:

Attesting Officer

BRUCE LEHMAN

Commissioner of Patents and Trademarks